United States Patent
Atthoff et al.

(10) Patent No.: US 8,945,173 B2
(45) Date of Patent: Feb. 3, 2015

(54) DORSAL FOREARM PLATE

(75) Inventors: Björn Atthoff, Uppsala (SE); Erik Hansson, Uppsala (SE); Fredrik Preinitz, Uppsala (SE); Fredrik Mahlin, Uppsala (SE)

(73) Assignee: St. Jude Medical Coordination Center BVBA, Zaventem (BE)

(*) Notice: Subject to any disclaimer, the term of this patent is extended or adjusted under 35 U.S.C. 154(b) by 480 days.

(21) Appl. No.: 13/379,541

(22) PCT Filed: Dec. 9, 2010

(86) PCT No.: PCT/EP2010/069244
§ 371 (c)(1),
(2), (4) Date: Dec. 20, 2011

(87) PCT Pub. No.: WO2011/073076
PCT Pub. Date: Jun. 23, 2011

(65) Prior Publication Data
US 2012/0101516 A1   Apr. 26, 2012

Related U.S. Application Data

(60) Provisional application No. 61/287,834, filed on Dec. 18, 2009.

(30) Foreign Application Priority Data

Dec. 18, 2009 (SE) ...................................... 0950988

(51) Int. Cl.
*A61B 17/00* (2006.01)
*A61G 15/12* (2006.01)
(Continued)

(52) U.S. Cl.
CPC ......... *A61B 17/1325* (2013.01); *A61F 5/05858* (2013.01)
USPC .............. 606/201; 128/877; 128/878; 602/20

(58) Field of Classification Search
CPC ............ A61F 5/05858; A61F 5/05866; A61F 5/3723; A61B 17/1325; A61G 13/1235; A61G 13/124
USPC ........... 606/201–204; 128/877–879; 602/5, 6, 602/20, 21
See application file for complete search history.

(56) References Cited

U.S. PATENT DOCUMENTS 2,529,786 A * 11/1950 Shaw ................................ 602/6
4,520,806 A * 6/1985 Miller .............................. 602/6
(Continued)

FOREIGN PATENT DOCUMENTS

EP   1 295 564 B1   3/2003
JP   2-109603 U   9/1990
(Continued)

OTHER PUBLICATIONS

Japanese Office Action, May 20, 2014, 6 pages.

*Primary Examiner* — Kathleen Holwerda
(74) *Attorney, Agent, or Firm* — Foley & Lardner LLP

(57) ABSTRACT

Dorsal forearm plate having a three-dimensional concave shape adapted to the shape of the dorsal forearm such that the dorsal forearm may rest on the forearm plate, the dorsal forearm plate has an essentially rectangular extension having opposing long sides and opposing short sides and has a substantially rigid unitary body adapted to underlie the posterior of the patient's hand, wrist and forearm, the plate is provided with two attachment bands, a distal and a proximal attachment band, adapted to attach the plate at the dorsal forearm of a patient. The shape of the side of the plate adapted to face the forearm during use, is adapted to the anatomy of the forearm in that it comprises two elongated depressions running in the longitudinal direction of the plate such that, during use of the plate, the ulnar bone and radius bone of the patient rest in the respective depression and that an elongated ridge, formed between the depressions, is adapted to extend into the softer tissue between the bones in order to orient and stabilize the forearm when attached to the plate. The invention also relates to a radial artery compression system comprising a dorsal forearm plate and a compression unit.

14 Claims, 5 Drawing Sheets

(51) Int. Cl.
*A61B 17/132* (2006.01)
*A61F 5/058* (2006.01)

(56) References Cited

U.S. PATENT DOCUMENTS

| | | | |
|---|---|---|---|
| 4,798,199 A | | 1/1989 | Hubbard et al. |
| 5,269,803 A | * | 12/1993 | Geary et al. ............... 606/201 |
| 5,601,597 A | | 2/1997 | Arrowood et al. |
| 5,695,520 A | * | 12/1997 | Bruckner et al. ............ 606/204 |
| 6,647,986 B1 | | 11/2003 | Korotko et al. |
| 7,498,477 B2 | | 3/2009 | Wada et al. |
| 2004/0039413 A1 | * | 2/2004 | Akerfeldt et al. ............ 606/201 |
| 2006/0211987 A1 | * | 9/2006 | Williams ..................... 604/116 |
| 2009/0131780 A1 | * | 5/2009 | O'Connor et al. ........... 600/407 |

FOREIGN PATENT DOCUMENTS

| | | |
|---|---|---|
| JP | 2001-61845 A | 3/2001 |
| JP | 2004-237004 A | 8/2004 |
| NL | 1016025 C2 | 3/2002 |
| WO | WO 91/05525 A1 | 5/1991 |
| WO | WO 2004/017841 A1 | 3/2004 |
| WO | WO 2008/013107 A1 | 1/2008 |

* cited by examiner

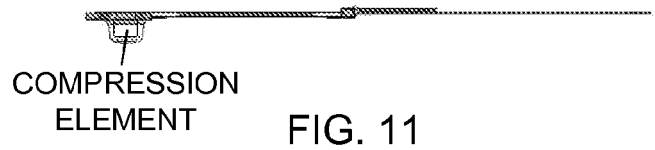
COMPRESSION
ELEMENT      FIG. 11
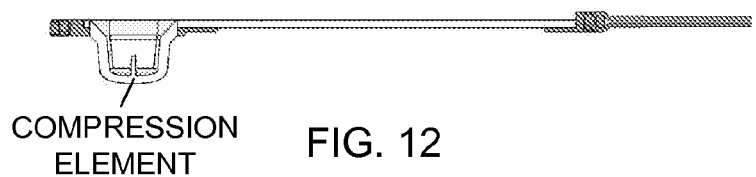
COMPRESSION
ELEMENT      FIG. 12
COMPRESSION
ELEMENT
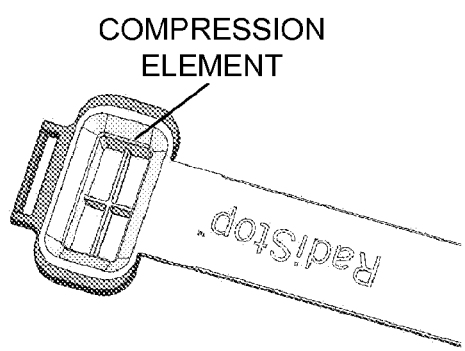
FIG. 13

DORSAL FOREARM PLATE

FIELD OF THE INVENTION

The present invention relates to a dorsal forearm plate and to a radial artery compression system, including a dorsal forearm plate and a compression unit, with which a compression force is applied on the radial artery such that haemostasis can be obtained.

BACKGROUND OF THE INVENTION

To access a patient's vascular system for an invasive medical procedure such as catheterization or similar procedures, a puncture is made in e.g. the femoral artery or the radial artery. The present invention is related to radial artery procedures. Following an invasive medical procedure, such as catheterisation or similar invasive medical procedure, the flow of blood through the puncture wound has to be stopped, so that haemostasis can begin as soon and fast as possible after the completion of the invasive medical procedure. Several devices have been suggested that facilitate and accelerate this haemostasis by providing a compression pressure that compresses blood vessels in various parts of the body to stop the flow of blood therethrough.

In the case of radial artery catheterisation, several radial artery occluders have been developed that stop the flow of blood through the puncture wound in the wrist by applying a compression force that occludes the radial artery. An illustrative example of such a pressure-applying device is disclosed in U.S. Pat. No. 5,601,597. This known artery occluder comprises a wrist splint, an adjustable securing strap attached to one end of the splint, and an adjustable pressure strap attached to the other end of the splint and provided with a pressure pad. When the artery occluder is mounted around the forearm of a patient, the wrist splint extends along the distal end of the forearm and the back of the wrist and hand, the securing strap extends around the palm of the hand, and the pressure strap extends around the distal end of the forearm, with the pressure pad being positioned over the puncture wound in the radial artery. During use of this occluder, the adjustable pressure strap is slowly tightened over the bleeding wound in the radial artery until the flow of blood in the radial artery has stopped at the wound. This aids haemostasis in the wound, but allows the ulnar artery to deliver enough blood to ensure tissue viability. In addition, the adjustable securing strap is tightened around the palm of the hand to help immobilize the wrist.

U.S. Pat. No. 6,647,986 shows a hand/wrist positioning splint to keep the hand positioned for radial artery access and to permit application of a haemostasis band. Two straps are used to secure the patient's hand to the splint and the haemostasis band comprises buckles to apply sufficient pressure to the puncture site.

U.S. Pat. No. 7,498,477 discloses a haemostatic device with a flexible band adapted to be wrapped around a patient's limb where bleeding is to be stopped at a puncture site. The band has a curved plate that is transparent to ensure the puncture site being visible through the band.

From WO 2004/017841 is a radial artery compression system known. The system comprises a splint with a supporting structure in order to hinder the splint to wobble when placed on a flat surface. Further, the system has three straps whereby one is a compression strap.

Another compression device for radial artery is shown in NL 1016025. The device uses two bands to secure the wrist and a third band is used to stop bleeding at a puncture site.

And finally, in U.S. Pat. No. 4,798,199, an arterial wrist support is disclosed used to support a patient's extremity for arterial or intravenous care that includes a substantial rigid, unitary moulded body adapted to matingly engage the patient's hand, wrist and at least a portion of the patient's forearm.

The inventors have realized that it is of great importance that the forearm is steadily fixated during the entire procedure such that the forearm bones, the radial and ulnar bones are held steady.

Thus, it is an object of the invention to provide an improved system that enables an accurately applied pressurization against a puncture site, and in particular enables a following adjustment of the applied pressure to the puncture site.

It is a further object of the invention to provide an improved system which is easy to handle and economical to manufacture and ship to the end user.

SUMMARY OF THE INVENTION

The above-mentioned objects are achieved by the present invention as defined by the independent claims.

Preferred embodiments are set forth in the dependent claims and in the detailed description.

Thus, the present invention is based upon the inventors' insight that by adapting the shape of the plate to the anatomy of the forearm, and in particular in relation to the distal parts of the forearm bones, the ulnar and radial bones, an improved stability is achieved.

The improvements achieved by the present invention may be summarized as follows:

The compression element is transparent for easier visibility over the puncture site that provides control over the puncture site, in terms of placement and detecting bleeding. The compression element is not stiff but is slightly flexible to provide a comfortable pressure. The dorsal forearm plate is fixating the wrist in a controlled position, minimizing bleeding complications and is comfortable for the patient and slimmer than previously used plates. In addition the plate prevents the patient to flex the wrist and cause late bleedings as well as reduces the risk for venous stasis.

The primary use for radial artery compression system according to the present invention is to achieve haemostasis after a transradial procedure. However, with the dorsal forearm plate, the cardiologist may also use the plate pre-, during and post procedure to fixate the wrist in a flexed position which allows easier access to the radial artery.

SHORT DESCRIPTION OF THE APPENDED DRAWINGS

Below the invention will be described with reference to the appended figures, of which:

in FIGS. 3-5.

FIG. 11 is a side view of the compression unit according to the present invention.

FIG. 12 is an enlarged cut-through side view of part of the compression unit according to the present invention.

FIG. 13 is a perspective view of a part of the compression unit according to the present invention showing the compression element.

DETAILED DESCRIPTION OF PREFERRED EMBODIMENTS OF THE INVENTION

Figure 1:
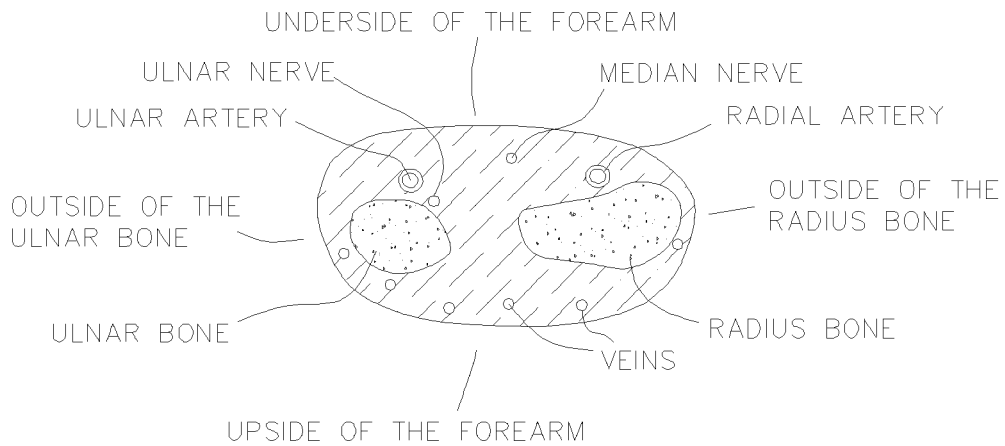
FIG. 1 is a schematic cross-sectional view of the wrist anatomy.
Figure 2:
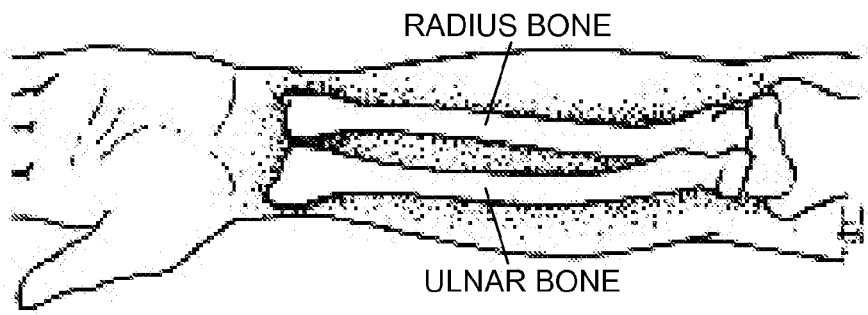
FIG. 2 shows schematically the forearm bones, the ulnar bone and the radius bone.

As background information, FIG. 1 shows schematically in cross-section the wrist anatomy with the ulnar and radius bones, the ulnar and radius arteries, the ulnar and median nerves, and the superficial veins at the upside of the forearm. In the description below, several references are made to different sides of the forearm, and also these terms are indicated in FIG. 1. FIG. 2 shows schematically the forearm bones, the ulnar bone and the radius bone, of the left forearm.

Figure 3:
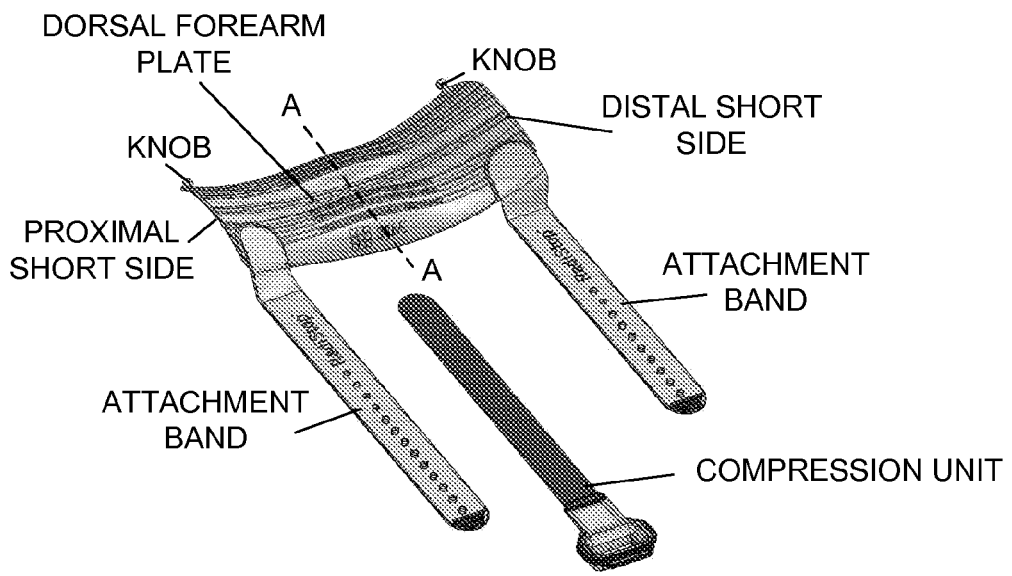
FIG. 3 is a perspective view of the radial compression system according to a first embodiment of the present invention.
Figure 4:
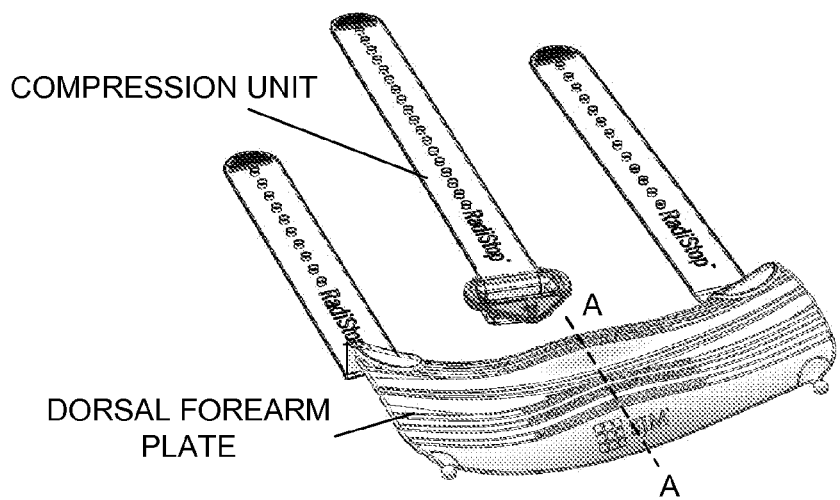
FIG. 4 is a perspective view of the radial compression system according to a second embodiment of the present invention.

FIGS. 3 and 4 show a dorsal forearm plate having a three-dimensional concave shape adapted to the shape of the dorsal forearm such that the dorsal forearm may rest on the forearm plate. The dorsal forearm plate has an essentially rectangular extension having opposing long sides and opposing short sides and has a substantially rigid unitary body adapted to underlie the posterior of the patient's hand, wrist and forearm. An exemplary width of the plate may be 6-9 cm and the length is in the interval of 15-23 cm. Naturally different sizes of the plate may be available, smaller ones to children and larger to adults and obese patients.

The plate is further provided with two attachment bands, a distal and a proximal attachment band, adapted to attach the plate at the dorsal forearm of a patient. These are preferably flexible. In the figure can be seen that the shape of the side of the plate is adapted to face the forearm during use and it is also adapted to the anatomy of the forearm in that it comprises two elongated depressions running in the longitudinal direction of the plate. These two depressions are aiming to, during use of the plate, that the ulnar bone and radius bone, in particular the distal parts of these bones, the so called styloid processes of each bone, of the patient rest in the respective depression and that an elongated ridge, formed between the depressions, is adapted to extend into the softer tissue between the bones in order to orient and stabilize the forearm when attached to the plate.

Figure 5:
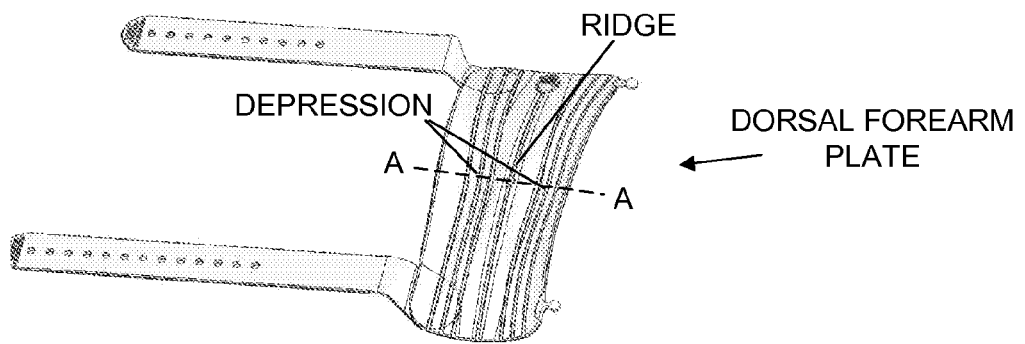
FIG. 5 is a perspective view showing the side facing the patient's forearm of the dorsal forearm plate according to the invention.

FIG. 5 is a perspective view showing the side facing the patient's forearm of the dorsal forearm plate according to the invention.

Figure 6:
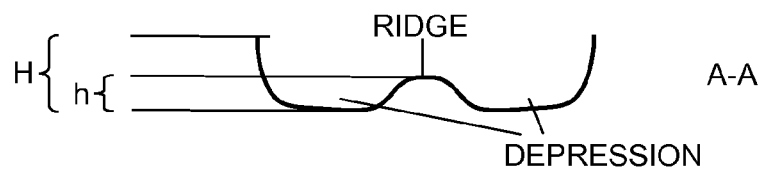
FIG. 6 is a schematic cross-sectional view of the dorsal forearm plate according to the present invention along A-A indicated e.g.

In order for the patient to comfortably rest and orient the forearm on the dorsal forearm plate the height of the elongated ridge at a cross-section A-A, essentially at a midpoint of the plate in the longitudinal direction, is at a level being in the interval of 10-50% of the total height of the plate at said cross-section A-A. The cross-section A-A is depicted e.g. in FIGS. 3-5. The height of the ridge is indicated as "h" in FIG. 6 and may be in the interval 5-15 mm and more specifically 6-9 mm, and the total height is indicated "H" which may be in the interval of 15-30 mm.

The dorsal forearm plate may be rigidly attached to the arm of the patient by the attachment bands provided with Velcro tape. The attachment bands may also be provided with holes and the plate provided with mating attachment knobs therefore. In the latter case, the band is preferably made at least partly of an elastic material to ensure a comfortable fit.

The dorsal forearm plate is essentially arc-shaped in the longitudinal direction such that it only rests on its short sides when arranged on a plane surface. Each of the short sides has an essentially straight supporting edge along a major part of its length and the supporting edges of said short sides are arranged in the same virtual plane. Thereby has the plate a stable support when used on a flat surface, e.g. a table. When the plate lies on a flat surface the midpoint of the plate is about 1 cm above the surface.

Figure 7:
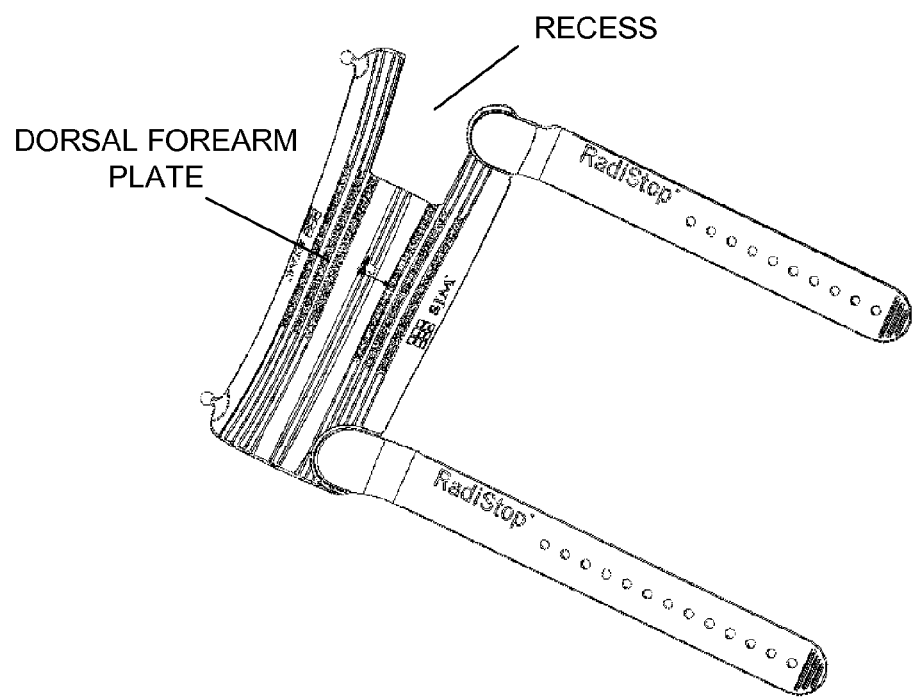
FIG. 7 is a perspective view from below of the dorsal forearm plate according to an alternative embodiment.
Figure 8:
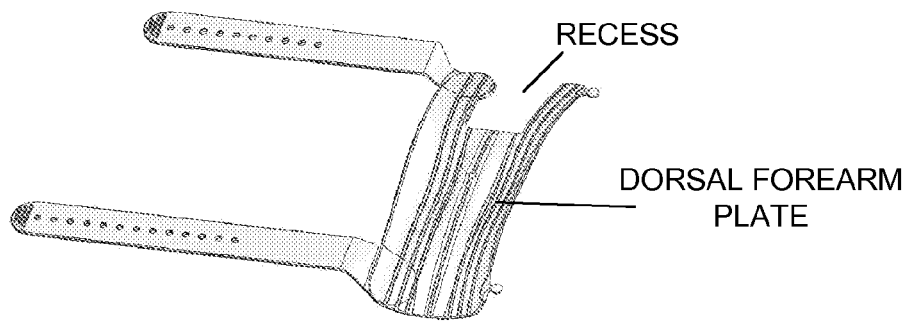
FIG. 8 is a perspective view from the side facing the patient's forearm of the dorsal forearm plate according to an alternative embodiment.

In order to e.g. gain access to blood vessels at the dorsal side of the hand the dorsal forearm plate is provided with a recess extending from the distal short side extending in the proximal direction such that an opening, having an essentially rectangular shape, is provided in the plate. This recess is shown in FIG. 7. FIG. 8 is a perspective view from the side facing the patient's forearm of the dorsal forearm plate according to the alternative embodiment.

The surface not intended to face the forearm of the plate is provided with a texture such that the friction is high and that said high friction surface extends at least along the mid third part of the plate. In e.g. FIG. 9 the texture is depicted.

Regarding the material of the dorsal forearm plate it may be made from pressure moulded plastic or any other suitable material that stabilizes the forearm. One preferred material is polypropylene. The attachment bands is preferably made from a thermoplastic elastomer.

According to the invention a radial artery compression system is provided that comprises a dorsal forearm plate as described above and a compression unit adapted to provide pressure to a radial artery puncture site as shown in e.g. FIGS. 3 and 4. The compression unit as further depicted in FIGS. 8-13 and comprises a compression element and a unit attachment band. The compression element has an elongated extension, defining a longitudinal axis of the element, in the direction of an artery to which it is to be applied. Further, the compression element is made from a transparent material, thereby providing the possibility of direct visual observation of the puncture wound, which facilitates the positioning of the compression element. Another distinctive feature of said element is that it is cup-shaped and has an outer convex surface, and is essentially rigid. The compression unit is adapted to be arranged around a patient's forearm where the dorsal forearm plate is attached and fixated, such that the compression element provides pressure to the puncture wound.

The radial artery compression system is further characterized by that the compression element has an essentially U-shaped cross-section perpendicular to the longitudinal axis which is clearly visible in the cross-sectional views of FIGS. 11 and 12. The shape of the compression element is clearly depicted in FIGS. 9-13, where it is seen that the element is provided with a lower flat surface that is adapted to be pressed against the puncture wound.

Figure 10:
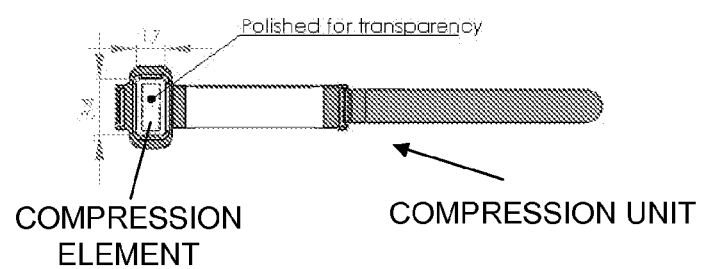
FIG. 10 is a top view of the compression unit according to the present invention.

In an exemplary embodiment the compression element has the size 17×34 mm which is indicated in FIG. 10.

Figure 9:
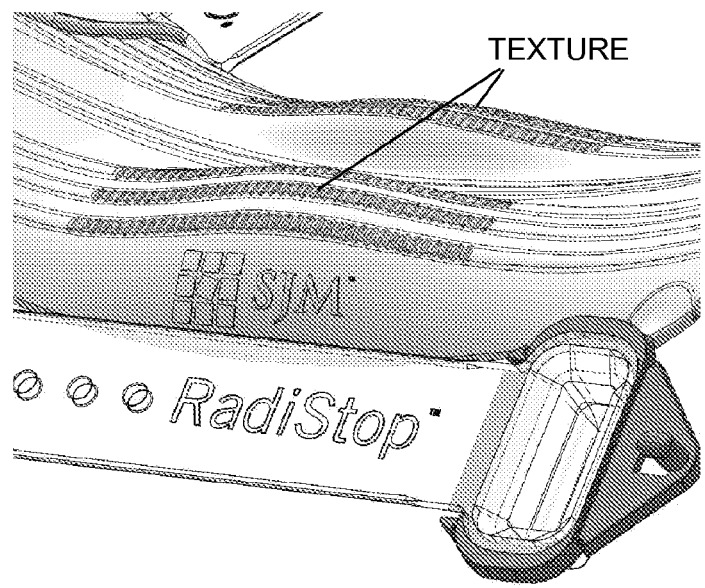
FIG. 9 show details of the compression element of the compression unit according to the present invention.

The compression element is arranged in an essentially rectangular frame and the said unit attachment band is fixated to one side of the frame, which can be seen in FIGS. 9 and 10. The compression element is preferably made from a termoplastic elastomer and may be pressure moulded as one unit together with the unit attachment band. In that case the frame is attached afterwards for stabilizing purposes.

The transparent compression element is preferably provided with indicating ribs, e.g. shaped as a cross as seen in FIG. 13, to indicate to the physician where to position the element in relation to the puncture wound. These ribs may also have a stabilizing purpose.

The unit attachment band of the radial artery compression system is provided with Velcro tape used to attach the unit to the forearm of a patient. The unit attachment band may also be provided with holes and the frame being then provided with a mating attachment knob. In the latter case, the band is preferably made of an elastic material. The unit attachment band can also be made partly of Velcro and partly of an elastic material, such as depicted in FIGS. 10-12.

When the forearm of the patient is readily fixed in the dorsal forearm plate by the attachment bands the puncture can be made and thereafter may the flow of blood from the puncture wound be stopped by applying the compression element to the puncture wound. Thereby, the blood flow is stopped directly and efficiently.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A device comprising:
a dorsal forearm plate comprising a substantially rigid unitary body having opposing long sides and opposing short sides, the dorsal forearm plate being configured to underlie a posterior of a hand, wrist, and forearm of a patient;
a plurality of attachment bands configured to attach the dorsal forearm plate to a dorsal forearm of the patient, the plurality of attachment bands including at least a distal attachment band and a proximal attachment band, wherein the dorsal forearm plate includes:
two elongated depressions extending in a longitudinal direction of the dorsal forearm plate and configured such that, during use of the device, an ulnar bone and a radius bone of the patient rest in respective ones of the elongated depressions, and
an elongated ridge formed between the depressions and configured such that, during use of the device, the elongated ridge presses into tissue between the ulnar bone and the radius bone to orient and stabilize the forearm, and
wherein the elongated depressions and the elongated ridge are integrally formed as parts of the rigid unitary body and, in a cross-section of the dorsal forearm plate that includes the elongated depressions and the elongated ridge, the dorsal forearm plate comprises a single material over an entirety of the dorsal forearm plate that is in said cross-section.

2. The device according to claim 1, wherein a height of the elongated ridge at a cross-section A-A essentially at a midpoint of the dorsal forearm plate in the longitudinal direction is at a level being in the interval of 10-50% of the total height of the dorsal forearm plate at said cross-section A-A.

3. The device according to claim 1, wherein said attachment bands comprise hook-and-loop fastener tape.

4. The device according to claim 1, wherein said attachment bands comprise holes and the dorsal forearm plate comprises mating attachment knobs.

5. The device according to claim 1, wherein the dorsal forearm plate is essentially arc shaped in the longitudinal direction such that the dorsal forearm plate rests only on the short sides when the dorsal forearm plate is arranged on a planar surface, and each of said short sides has an essentially straight supporting edge, said supporting edges of said short sides being arranged in the same virtual plane.

6. The device according to claim 1, wherein the dorsal forearm plate includes an essentially rectangular recess extending from the distal short side in the proximal direction.

7. The device according to claim 1, wherein a surface of the dorsal forearm plate that is not intended to face the forearm has a textured surface extending at least along a mid third part of the dorsal forearm plate.

8. The device according to claim 1, wherein the dorsal forearm plate is made from pressure moulded plastic.

9. The device of claim 1, further comprising:
a compression unit configured to provide pressure to a puncture site, the compression unit comprising:
a compression element; and
an attachment band attached to the compression element,
wherein the compression element has a length in a direction of an artery to which the compression element is configured to be applied, and a width perpendicular to the length, the length being greater than the width,
wherein the compression element is made from a transparent material configured to allow direct visual observation of the puncture site,
wherein the compression element is cup-shaped and has an outer convex surface, and is essentially rigid, and
wherein the compression unit is configured to be arranged around the forearm of the patient at a location where said dorsal forearm plate is attached, such that the compression element provides pressure to the puncture site.

10. The device according to claim 9, wherein the compression element has an essentially U-shaped cross-section perpendicular to said longitudinal direction.

11. The device according to claim 9, wherein the compression element is arranged in an essentially rectangular frame, and said attachment band is fixated to a side of the frame.

12. The device according to claim 9, wherein the attachment band includes hook-and-loop fastener tape configured to be used to attach the compression unit to the forearm of the patient.

13. The device according to claim 11, wherein said attachment band comprises holes and the frame comprises a mating attachment knob.

14. The device according to claim 1, wherein, in said cross-section of the dorsal forearm plate that includes the elongated depressions and the elongated ridge, the dorsal forearm plate has a uniform material thickness over an entirety of the dorsal forearm plate that is in said cross-section.

* * * * *